US012576092B2

(12) United States Patent (10) Patent No.: US 12,576,092 B2
Bhatia et al. (45) Date of Patent: Mar. 17, 2026

(54) PHARMACEUTICAL SUSPENSIONS FOR BISMUTH SUBSALICYLATES

(71) Applicant: L. Perrigo Company, Allegan, MI (US)

(72) Inventors: Inderdeep S. Bhatia, Kalamazoo, MI (US); David R. Cassiday, Caledonia, MI (US); Bruce D. Johnson, Byron Center, MI (US); Carlos O. Paz, Fairview, NJ (US)

(73) Assignee: L. PERRIGO COMPANY, Allegan, MI (US)

( * ) Notice: Subject to any disclaimer, the term of this patent is extended or adjusted under 35 U.S.C. 154(b) by 0 days.

(21) Appl. No.: 18/136,443

(22) Filed: Apr. 19, 2023

(65) Prior Publication Data

US 2023/0270758 A1 Aug. 31, 2023

Related U.S. Application Data

(63) Continuation of application No. 16/641,564, filed as application No. PCT/US2018/047966 on Aug. 24, 2018, now abandoned.

(60) Provisional application No. 62/550,143, filed on Aug. 25, 2017.

(51) Int. Cl.
| | |
|---|---|
| *A61K 31/625* | (2006.01) |
| *A61K 9/08* | (2006.01) |
| *A61K 47/36* | (2006.01) |
| *A61K 47/38* | (2006.01) |

(52) U.S. Cl.
CPC .............. *A61K 31/625* (2013.01); *A61K 9/08* (2013.01); *A61K 47/36* (2013.01); *A61K 47/38* (2013.01)

(58) Field of Classification Search
CPC ...... A61P 1/04; A61P 1/12; A61P 1/00; A61K 9/0095; A61K 31/60; A61K 31/625; A61K 33/245; A61K 47/36; A61K 47/38; A61K 9/08; A61K 2300/00; A61K 31/4439; A61K 47/12; A61K 9/0056; A61K 9/107; A61K 9/14; A61K 9/1617; A61K 9/2013; A61K 9/2018; A61K 9/2027; A61K 9/2054; A61K 9/2081; A61K 9/2846; A61K 9/2886; A61K 9/5026; A61K 9/5078; A61K 45/06; A61K 31/10; A61K 31/165; A61K 31/19; A61K 31/192; A61K 31/7008; A61K 31/726; A61K 31/737; A61K 47/02; A61K 9/006; A61K 9/0063; A61K 9/2009; A61K 9/2086
See application file for complete search history.

(56) References Cited

U.S. PATENT DOCUMENTS

| | | | |
|---|---|---|---|
| 4,801,454 | A | 1/1989 | Coveney |
| 4,940,695 | A | 7/1990 | Coveney et al. |
| 5,013,560 | A | 5/1991 | Stentz et al. |
| 5,244,670 | A | 9/1993 | Upson et al. |
| 5,759,579 | A | 6/1998 | Singh et al. |
| 9,486,436 | B2 | 11/2016 | Gilbert et al. |
| 9,486,460 | B2 | 11/2016 | White, Jr. et al. |
| 2003/0215524 | A1* | 11/2003 | Pena ........................ A61P 1/00 |
| | | | 424/653 |
| 2009/0003123 | A1 | 1/2009 | Morrison, Jr. et al. |
| 2015/0306061 | A1 | 10/2015 | Gilbert et al. |
| 2015/0306113 | A1 | 10/2015 | White, Jr. et al. |

FOREIGN PATENT DOCUMENTS

| | | | | | |
|---|---|---|---|---|---|
| CN | 100528232 | C | * | 8/2009 | ......... A61K 31/4439 |
| EP | 0166440 | A2 | | 1/1986 | |
| EP | 0217440 | A1 | | 4/1987 | |
| WO | 9824455 | A1 | | 6/1998 | |

OTHER PUBLICATIONS

CN-100528232-C_translation (Year: 2009).*
PCT/US2018/047966 International Search Report dated Nov. 28, 2018.

* cited by examiner

*Primary Examiner* — Audrea B Coniglio
(74) *Attorney, Agent, or Firm* — Honigman LLP; Christopher C. Forbes

(57) ABSTRACT

The invention is directed to pharmaceutical compositions for suspending bismuth subsalicylate and methods of use thereof. Formulations of the present invention include at least three-gum systems to prevent the settling out of heavy particles in solution and do not include magnesium aluminum silicate. The pharmaceutical compositions may be used to treat gastrointestinal disorders.

4 Claims, 15 Drawing Sheets

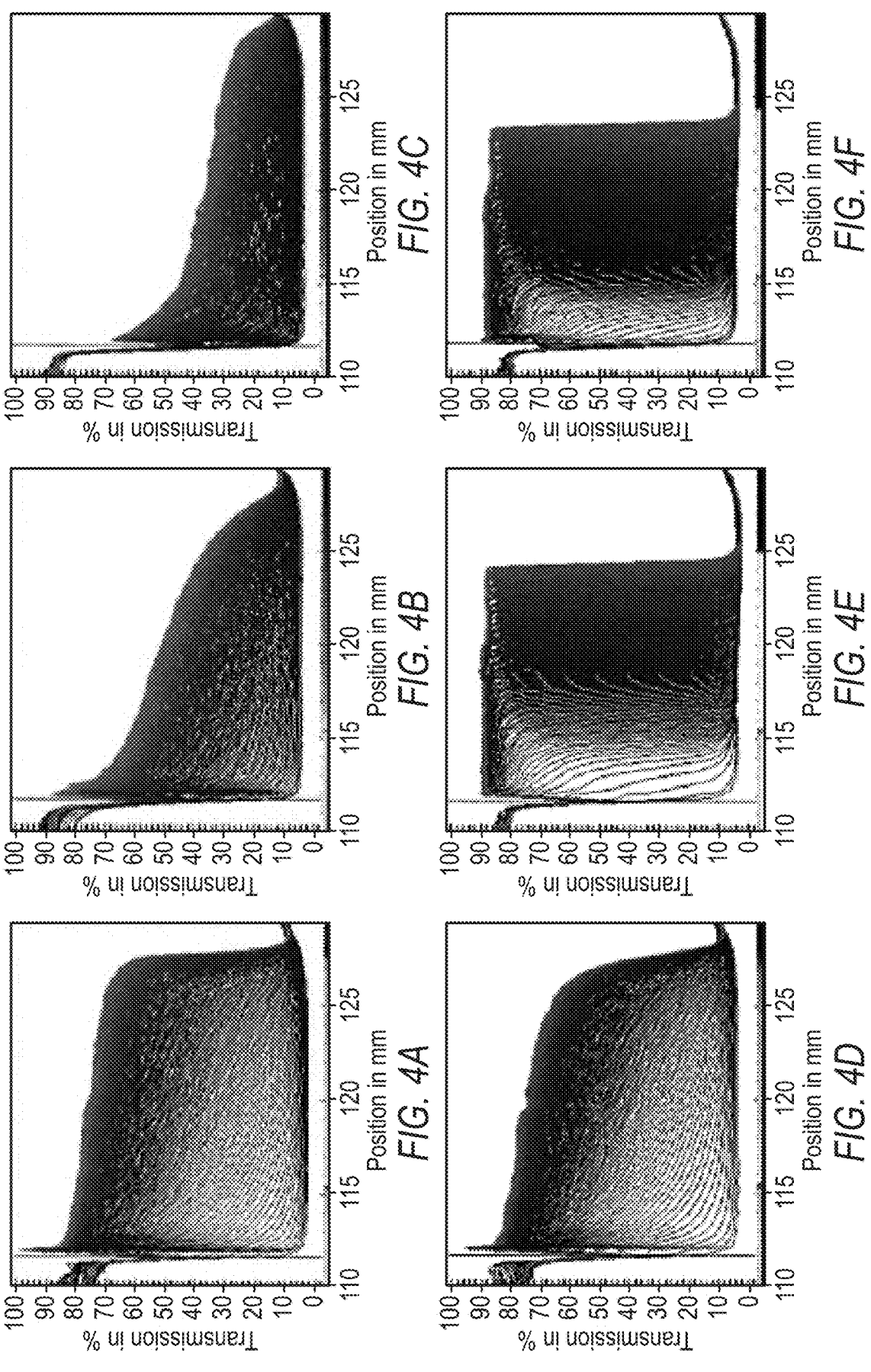

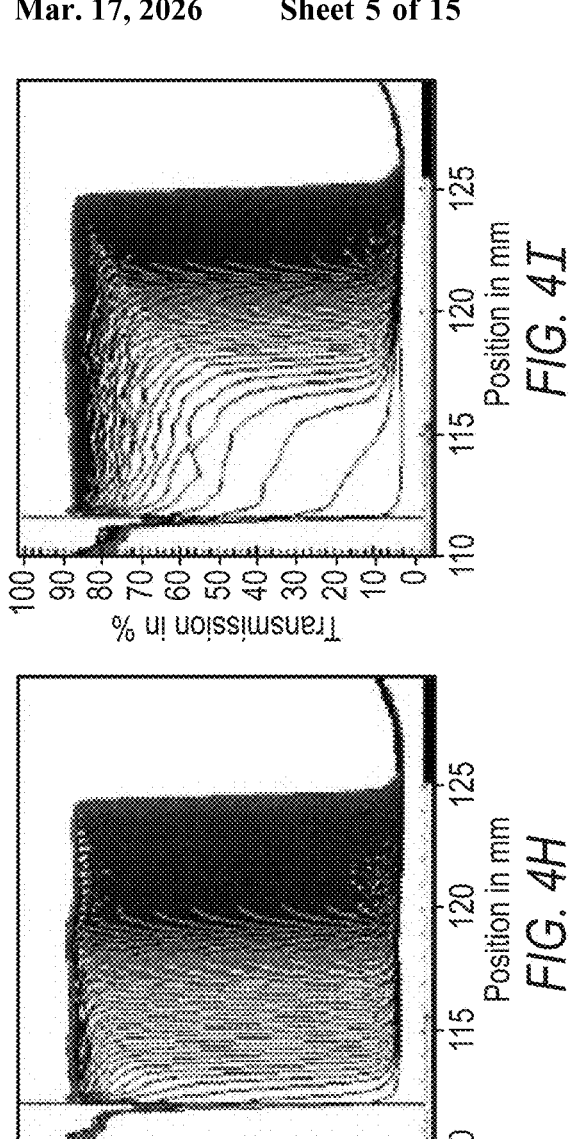
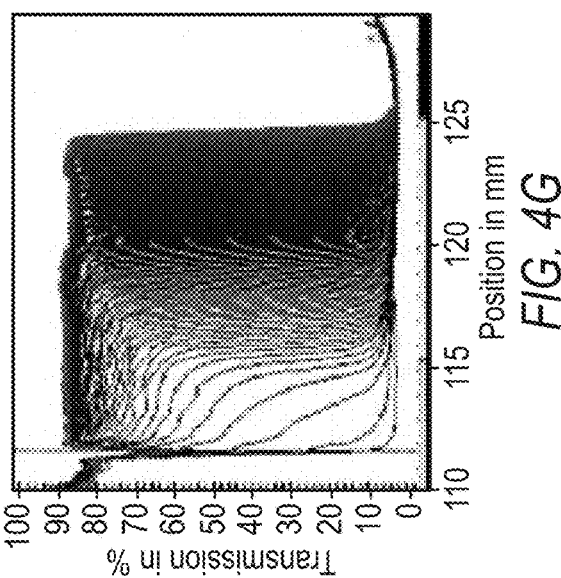

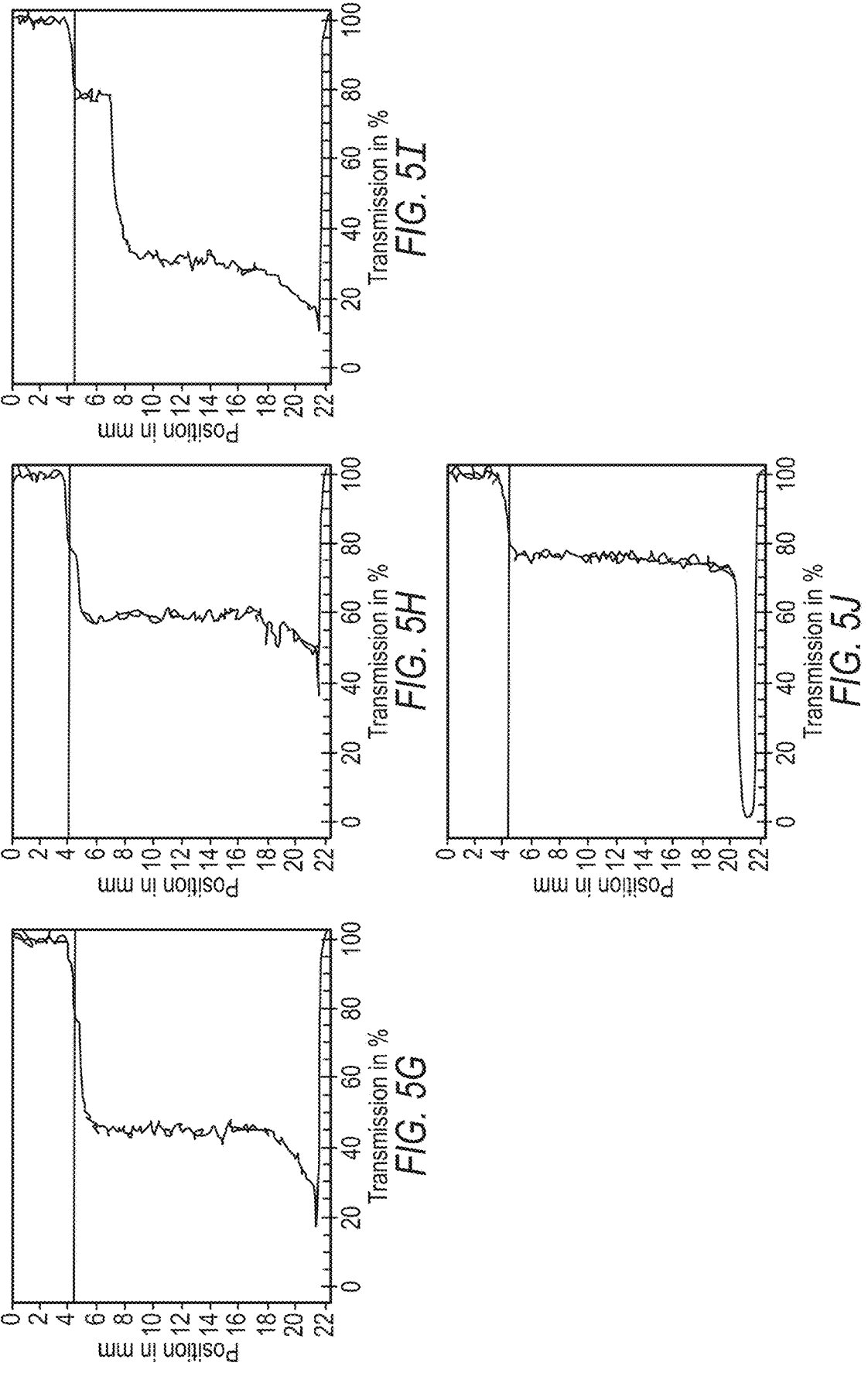

PHARMACEUTICAL SUSPENSIONS FOR BISMUTH SUBSALICYLATES

CROSS-REFERENCE TO RELATED APPLICATIONS

This application is a Continuation application and claims priority to U.S. patent application Ser. No. 16/641,564 which is a National Stage Application and claims priority under 35 U.S.C. § 371 to Patent Cooperation Treaty application PCT/US2018/047966, filed Aug. 24, 2018, which claims the benefit of U.S. Provisional Application No. 62/550,143, filed Aug. 25, 2017. Priority is claimed to these applications and the disclosures of these prior applications are considered part of the disclosure of this application, and to the extent allowed, the entire contents of the aforementioned applications are incorporated herein.

FIELD OF INVENTION

The invention is directed to pharmaceutical compositions for suspending bismuth subsalicylate and methods of use thereof. Formulations of the present invention include three-gum systems to prevent the settling out of heavy particles. The pharmaceutical compositions may be used to treat gastrointestinal disorders.

BACKGROUND OF THE INVENTION

Bismuth subsalicylate has been used for decades for the relief of gastrointestinal disorders such as upset stomach and diarrhea. Bismuth subsalicylate is typically found in a suspension using magnesium aluminum silicate as part of the gum system. Bismuth subsalicylate is a heavy material that is difficult to keep in suspension, and is difficult to re-suspend once it has settled at the bottom of a bottle. To date, most commercial formulations of bismuth subsalicylate have been suspended with the aid of magnesium aluminum silicate.

However, magnesium aluminum silicate is a mined clay and may contain trace amounts of lead. There is a desire to minimize the lead in pharmaceutical compositions.

Previous formulations of bismuth subsalicylate with reduced magnesium aluminum silicate are described in U.S. Pat. Nos. 9,486,640 and 9,486,436. U.S. Pat. No. 9,486,460 describes a bismuth-containing pharmaceutical agent, gellan gum and magnesium aluminum silicate. U.S. Pat. No. 9,486,436 describes complex manufacturing methods for making pharmaceutical suspensions with magnesium aluminum silicate, gellan gum, bismuth, and methyl cellulose.

Disclosed herein are pharmaceutical compositions that are three-gum systems without magnesium aluminum silicate. Accordingly, the compositions described herein minimize the use of magnesium aluminum silicate without sacrificing the ability of the compositions to keep the bismuth subsalicylate in suspension.

SUMMARY OF THE INVENTION

The present invention includes pharmaceutical compositions and methods of treating gastrointestinal disorders using pharmaceutical compositions. In one aspect of the invention, the composition comprises bismuth subsalicylate, microcrystalline cellulose, xanthan gum, and an excipient selected from the group consisting of: carboxymethyl cellulose (CMC), carageenan, and hydroxyethyl cellulose (HEC), or combinations thereof.

In another aspect of the invention, pharmaceutical compositions comprising bismuth subsalicylate may be used to treat gastrointestinal disorders. In some embodiments, the gastrointestinal disorder is selected from diarrhea, indigestion, heartburn, and nausea.

BRIEF DESCRIPTION OF THE DRAWINGS

FIGS. 4A-4I show dispersion fingerprints of pharmaceutical compositions taken with LUMiSizer® using STEP technology according to an embodiment of the present invention.

FIGS. 5A-5J show a sediment formation analysis as determined by X-Ray analysis using LUMiReader® X-Ray equipment of pharmaceutical formulations at 23° C. according to an embodiment of the present invention.

DETAILED DESCRIPTION OF THE INVENTION

Figure 1:
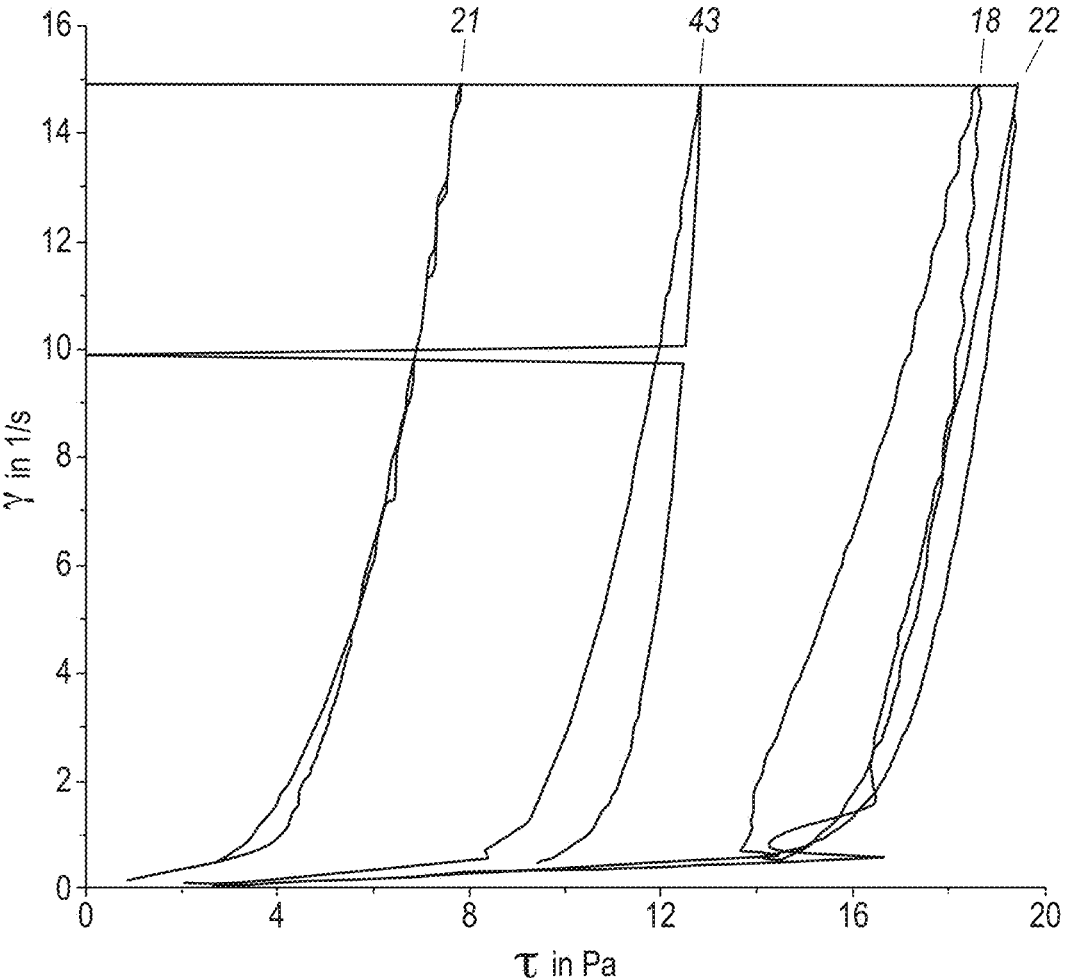
FIG. 1 shows a rheogram comparing sample compositions 18, 21, 22, and 43 according to an embodiment of the present invention

As used herein, the term "three-gum system" refers to a suspension composition according to the present invention, wherein the composition includes at least three different polysaccharide-based thickening agents. Examples of thickening agents include, but are not limited to, agar, alginic acid, carrageenan, corn starch, carboxymethyl cellulose (CMC), hydroxyethyl cellulose (HEC), guar gum, hydroxypropyl cellulose, hypromellose (hydroxypropyl methyl cellulose), methylcellulose, pectin, sodium alginate, tragacanth, and xanthan gum.

The pharmaceutical compositions of the present invention provide a suspension formulation for minimizing heavy particle sedimentation in solution. In one aspect of the invention, the composition comprises bismuth subsalicylate, microcrystalline cellulose, xanthan gum, and an excipient selected from the group consisting of: carboxymethyl cellulose, carageenan, and hydroxyethyl cellulose, or combinations thereof. In another aspect of the invention, the composition comprises bismuth subsalicylate, Avicel®RC-591, xanthan gum, and hydroxyethyl cellulose.

Pharmaceutical compositions of the present invention comprise bismuth subsalicylate. Bismuth subsalicylate is known to treat temporary gastrointestinal disorders such as diarrhea, indigestion, heartburn, and nausea. In some embodiments, the pharmaceutical composition comprises bismuth subsalicylate in an amount of from about 10 mg/mL to about 60 mg/mL. In some embodiments, the pharmaceutical composition comprises bismuth subsalicylate in an amount of from 17.5 mg/mL to about 53.0 mg/mL. In some embodiments, the pharmaceutical composition comprises bismuth subsalicylate in an amount of from about 15 mg/mL to about 20 mg/mL. In further embodiments, the pharmaceutical composition comprises bismuth subsalicylate in an amount of about 17.5 mg/mL.

In some embodiments, pharmaceutical compositions of the present invention may contain a double dose of bismuth subsalicylate. In some embodiments, the pharmaceutical composition comprises bismuth subsalicylate in an amount of from about 32.5 mg/mL to about 37.5 mg/mL.

In some embodiments, pharmaceutical compositions of the present invention may contain a triple does of bismuth subsalicylate. In some embodiments, the pharmaceutical composition comprises bismuth subsalicylate in an amount of from about 50 mg/mL to about 55 mg/mL. In further embodiments, the pharmaceutical composition comprises bismuth subsalicylate in an amount of about 52.5 mg/mL.

In some embodiments, the pharmaceutical composition does not comprise magnesium aluminum silicate. Magnesium aluminum silicate is a mined clay, and may contain traces of lead. There is a desire to minimize lead in pharmaceutical compositions. Pharmaceutical compositions of the present invention have been formulated to suspend heavy particles of bismuth subsalicylate without using magnesium aluminum silicate.

In some embodiments, the pharmaceutical composition comprises hydroxyethyl cellulose. In some embodiments, the pharmaceutical composition comprises hydroxyethyl cellulose in an amount of from about 0.10 mg/mL to about 1.5 mg/mL. In some embodiments, the pharmaceutical composition comprises hydroxyethyl cellulose in an amount of from about 0.45 mg/mL to about 0.95 mg/mL. In some embodiments, the pharmaceutical composition comprises hydroxyethyl cellulose in an amount of about 0.88 mg/mL. In some embodiments, the pharmaceutical composition comprises hydroxyethyl cellulose in an amount of from about 1.0 mg/mL to about 2.0 mg/mL. In some embodiments, the pharmaceutical composition comprises hydroxyethyl cellulose in an amount of from about 1.25 mg/mL to about 1.75 mg/mL. In some embodiments, the pharmaceutical composition comprises hydroxyethyl cellulose in an amount of about 1.5 mg/mL.

In some embodiments, the pharmaceutical composition comprises carboxymethyl cellulose. In some embodiments, carboxymethyl cellulose is added to change the viscosity of the pharmaceutical composition. Without being bound to any particular theory, it is believed that there is an interaction between salicylates and carboxymethyl cellulose which may affect the viscosity and pH of the pharmaceutical composition. In other embodiments, the carboxymethyl cellulose is carboxymethyl cellulose 9.

In some embodiments, the composition comprises Avicel® RC-591 (AVICEL). AVICEL RC-591 is a mixture of sodium carboxymethyl cellulose and microcrystalline cellulose. AVICEL RC-591 is a water dispersible organic hydrocolloid used in the preparation of pharmaceutical suspensions and emulsions. The colloidal microcrystalline cellulose may provide a structured dispersion vehicle while the carboxymethyl cellulose may facilitate dispersion and serve as a protective colloid. In some embodiments, the pharmaceutical composition comprises AVICEL RC-591 in an amount of from about 10 mg/mL to about 30 mg/mL. In some embodiments, the pharmaceutical composition comprises AVICEL RC-591 in an amount of from about 14 mg/mL to about 20 mg/mL. In some embodiments, the pharmaceutical composition comprises AVICEL RC-591 in an amount of about 17.1 mg/mL. In some embodiments, the pharmaceutical composition comprises AVICEL RC-591 in an amount of about 17.5 mg/mL.

Pharmaceutical compositions of the present invention may comprise xanthan gum. Xanthan gum may be used to prevent separation of components in pharmaceutical compositions. Xanthan gum is also known to suspend solid particles. In some embodiments, the pharmaceutical composition comprises xanthan gum in an amount of from about 0.50 mg/mL to about 5.0 mg/mL. In some embodiments, the pharmaceutical composition comprises xanthan gum in an amount of from about 1.5 mg/mL to about 3.5 mg/mL. In some embodiments, the pharmaceutical composition comprises xanthan gum in an amount of about 2.0 mg/mL. In some embodiments, the pharmaceutical composition comprises xanthan gum in an amount of about 2.9 mg/mL.

In some embodiments, the pharmaceutical composition comprises simethicone or a simethicone emulsion. In some embodiments, simethicone is added to the pharmaceutical composition to improve mouthfeel. In some embodiments, simethicone is added to the pharmaceutical composition to reduce foaming. In some embodiments, the pharmaceutical composition comprises simethicone in an amount of from about 0.001 mg/mL to about 0.02 mg/mL. In some embodiments, the pharmaceutical composition comprises simethicone in an amount of about 0.01 mg/mL.

In some embodiments of the invention, the pharmaceutical composition may contain a mixture of carboxymethyl cellulose and microcrystalline cellulose. In some embodiments the pharmaceutical composition may contain a ratio of the mixture of carboxymethyl cellulose and microcrystalline cellulose to xanthan gum from about 2:1 to about 20:1. In other embodiments, the ratio of the mixture of carboxymethyl cellulose and microcrystalline cellulose to xanthan gum is from about 4:1 to about 15:1.

The LUMiSizer employs Step-technology to measure across the whole sample instantaneously. Like human fingerprints, suspensions also have unique fingerprints based on their interactions with light at specified wavelengths. The pharmaceutical compositions of the present invention have a unique fingerprint compared to other samples.

It is an object of the present invention to prevent sedimentation of particulates in a pharmaceutical composition. Sedimentation rates may be determined using LUMiReader X-Ray using STEP technology. STEP technology obtains Space- and Time-resolved Extinction Profiles over the length of the sample. In a STEP analysis, parallel light is transmitted through a sample and is detected by sensors to determine particle concentration. STEP analysis also includes placing samples in a centrifuge to simulate composition settling over time. In some embodiments, pharmaceutical compositions of the present invention may be analyzed at 23° C. In some embodiments, pharmaceutical compositions of the present invention have sedimentation rates of from about 0.001 mm/day to about 0.012 mm/day at 23° C. as determined by X-Ray measurement.

Pharmaceutical compositions of the present invention have an appropriate viscosity. If a solution is too viscous, it is difficult to administer and has a poor mouthfeel. Similarly, pharmaceutical compositions with low viscosities may be "watery" or "chalky" and have a poor mouthfeel and may result in sedimentation. In some embodiments, pharmaceutical compositions of the present invention have a viscosity of from about 600 cps to about 2000 cps. In some embodiments, the pharmaceutical composition has a viscosity of from about 900 cps to about 1400 cps. Viscosity determinations for compositions of the present invention were taken using a Brookfield Viscometer DV-I Prime at a speed of 30 RPM using a LV3 spindle.

Pharmaceutical compositions of the present invention preferably have a pH value of from about 4 to about 5. In some embodiments, the pharmaceutical composition has a pH of from about 4.1 to about 4.6. In some embodiments, the pharmaceutical composition has a pH of from about 4.3 to about 4.4.

In some embodiments, the ratio of carboxymethyl cellulose to total salicylates in the pharmaceutical composition is adjusted to change one or more of pH and viscosity. Yield value is a measurable quantity similar to, but not dependent on, viscosity. It can be thought of as the initial resistance to flow under stress, hence, it is also referred to as yield stress. Particles dispersed in a medium will remain suspended if the yield value of the medium is sufficient to overcome the effect of gravity or buoyancy on those particles. Yield value was measured using Thermo-Haake Rheostress.

In some embodiments, the pharmaceutical composition of the present invention achieves or approaches a yield value while remaining a flowable (not gelatinous) composition.

In another aspect of the invention, a pharmaceutical composition may comprise:
  a) bismuth subsalicylate;
  b) a mixture of microcrystalline cellulose and carboxymethyl cellulose;
  c) xanthan gum; and
  d) hydroxyethyl cellulose.

In some embodiments of the invention, the pharmaceutical composition may comprise a ratio of the mixture of microcrystalline cellulose and carboxymethyl cellulose to hydroxyethyl cellulose from about 3:1 to about 300:1. In other embodiments, the ratio of the mixture of microcrystalline cellulose and carboxymethyl cellulose to hydroxyethyl cellulose is from about 6:1 to about 250:1.

In some embodiments, the ratio of the mixture of microcrystalline cellulose and carboxymethyl cellulose to xanthan gum is from about 3:1 to about 15:1. In other embodiments, the ratio of the mixture of microcrystalline cellulose and carboxymethyl cellulose to xanthan gum is from about 5:1 to about 13:1.

In some embodiments, the pharmaceutical composition contains a ratio of xanthan gum to hydroxyethyl cellulose from about 1:1 to about 40:1. In other embodiments, the ratio of xanthan gum to hydroxyethyl cellulose is from about 1.3:1 to about 20:1.

In another aspect of the invention, pharmaceutical compositions comprising bismuth subsalicylate may be used to treat gastrointestinal disorders. In some embodiments, the gastrointestinal disorder is selected from diarrhea, indigestion, heartburn, and nausea.

In one aspect, the invention includes a pharmaceutical composition comprising:
  a) bismuth subsalicylate;
  b) microcrystalline cellulose;
  c) xanthan gum; and d) an excipient selected from the group consisting of: carboxymethyl cellulose, carrageenan, and hydroxyethyl cellulose, or combinations thereof.

In one embodiment, the composition consists essentially of:
  a) bismuth subsalicylate;
  b) microcrystalline cellulose;
  c) xanthan gum; and
  d) an excipient selected from the group consisting of: carboxymethyl cellulose, carrageenan, and hydroxyethyl cellulose, or combinations thereof.

In one embodiment, said excipient is hydroxyethyl cellulose.

In one embodiment, said composition comprises bismuth subsalicylate in an amount of from about 10 mg/mL to about 60 mg/mL.

In a further embodiment, said composition comprises bismuth subsalicylate in an amount of from about 17.5 mg/mL to about 53 mg/mL.

In another further embodiment, said composition comprises bismuth subsalicylate in an amount of from about 15 mg/mL to about 20 mg/mL.

In still a further embodiment, said composition comprises bismuth subsalicylate in an amount of about 17.5 mg/mL.

In another embodiment, said composition comprises bismuth subsalicylate in an amount of about 32.5 mg/mL to about 37.5 mg/mL.

In another further embodiment, said composition comprises bismuth subsalicylate in an amount of about 35 mg/mL.

In another embodiment, said composition comprises bismuth subsalicylate in an amount of about 52.5 mg/mL.

In one embodiment, said composition comprises carboxymethyl cellulose and hydroxyethyl cellulose.

In one embodiment, said composition comprises xanthan gum in an amount of from about 0.50 mg/mL to about 5.0 mg/mL.

In a further embodiment, said composition comprises xanthan gum in an amount of from about 1.0 mg/mL to about 3.0 mg/mL.

In a further embodiment, said composition comprises xanthan gum in an amount of about 2.0 mg/mL.

In another further embodiment, said composition comprises xanthan gum in an amount of about 2.9 mg/mL.

In one embodiment, said composition comprises hydroxyethyl cellulose in an amount of from about 0.45 mg/mL to about 2.0 mg/mL.

In a further embodiment, said composition comprises hydroxyethyl cellulose in an amount of about 1.5 mg/mL.

In one embodiment, said composition comprises a mixture of carboxymethyl cellulose and microcrystalline cellulose.

In a further embodiment, the mixture of carboxymethyl cellulose and microcrystalline cellulose is present in an amount of from about 14 mg/mL to about 20 mg/mL.

In one embodiment, the mixture of carboxymethyl cellulose and microcrystalline cellulose comprises a spray dried blend of carboxymethyl cellulose and microcrystalline cellulose.

In a further embodiment, the mixture of carboxymethyl cellulose and microcrystalline cellulose is present in an amount of about 17.1 mg/mL.

In another further embodiment, the mixture of carboxymethyl cellulose and microcrystalline cellulose is present in an amount of about 17.5 mg/mL.

In one embodiment, the ratio of the mixture of carboxymethyl cellulose and microcrystalline cellulose to xanthan gum is from about 2:1 to about 20:1.

In a further embodiment, the ratio of the mixture of carboxymethyl cellulose and microcrystalline cellulose to xanthan gum is from about 4:1 to about 15:1.

In one embodiment, said composition has a sedimentation rate of from about 0.001 mm/day to about 0.015 mm/day at 23° C. as determined by x-ray measurement.

In a further embodiment, said composition has a sedimentation rate of from about 0.001 mm/day to about 0.012 mm/day at 23° C. as determined by x-ray measurement.

In one embodiment, said composition has a viscosity of from about 800 cps to about 2400 cps.

In a further embodiment, said composition has a viscosity of from about 1200 cps to about 2000 cps.

In one embodiment, the pH of the composition is from about 4.0 to about 5.5.

In a further embodiment, the pH of the composition is from about 4.9 to about 5.0.

In another further embodiment, the pH of the composition is from about 4.3 to about 4.4.

In another aspect, the invention includes a pharmaceutical composition comprising:
a) bismuth subsalicylate;
b) xanthan gum;
c) hydroxyethyl cellulose; and
d) a mixture of microcrystalline cellulose and carboxymethyl cellulose.

In one embodiment, the ratio of the mixture of microcrystalline cellulose and carboxymethyl cellulose to hydroxyethyl cellulose is from about 6:1 to about 250:1.

In a further embodiment, the ratio of the mixture of microcrystalline cellulose and carboxymethyl cellulose to hydroxyethyl cellulose is from about 11:1 to about 12:1.

In still a further embodiment, the ratio of the mixture of microcrystalline cellulose and carboxymethyl cellulose to xanthan gum is from about 5:1 to about 13:1.

In still a further embodiment, the ratio of the mixture of microcrystalline cellulose and carboxymethyl cellulose to xanthan gum is from about 5.5:1 to about 6.5:1.

In one embodiment, the ratio of xanthan gum to hydroxyethyl cellulose is from about 1.3:1 to about 20:1.

In a further embodiment, the ratio of xanthan gum to hydroxyethyl cellulose is from about 1.9:1 to about 2.0:1.

In one embodiment, the mixture of carboxymethyl cellulose and microcrystalline cellulose comprises a spray dried blend of carboxymethyl cellulose and microcrystalline cellulose.

In one embodiment, the mixture of carboxymethyl cellulose and microcrystalline cellulose is commercially available as AVICEL RC-591.

In another aspect, the invention includes an aqueous pharmaceutical composition comprising:
a) about 35 mg/mL glycerin;
b) about 0.01 mg/mL simethicone;
c) about 1.5 mg/mL hydroxyethyl cellulose;
d) about 2.9 mg/mL xanthan gum;
e) about 17.5 mg/mL of a mixture of carboxymethyl cellulose and microcrystalline cellulose;
f) from about 15 mg/mL to about 37 mg/mL bismuth subsalicylate;
g) about 0.2 mg/mL salicylic acid;
h) about 0.01 mg/mL sodium salicylate;
i) about 0.41 mg/mL sodium saccharin;
j) about 0.35 mg/mL potassium sorbate;
k) about 1.0 mg/mL methylsalicylate;

l) from about 0.05 mg/mL to about 0.07 mg/mL Red #22D&C; and
m) about 0.045 mg/mL to about 0.14 mg/mL Red #28D&C.

In a further embodiment, the concentration of bismuth subsalicylate is about 17.5 mg/mL, the concentration of Red #22 D&C is about 0.0563 mg/mL, and the concentration of Red #28 D&C is about 0.04814 mg/mL.

In another further embodiment, the concentration of bismuth subsalicylate is about 35.0 mg/mL, the concentration of Red #22 D&C is about 0.06777 mg/mL, and the concentration of Red #28 D&C is about 0.1304 mg/mL.

In another aspect, the invention includes a method of treating a gastrointestinal disorder in a patient in need thereof, comprising administering to the patient a composition comprising:
a) bismuth subsalicylate;
b) microcrystalline cellulose;
c) xanthan gum; and
d) an excipient selected from the group consisting of: carboxymethyl cellulose, carrageenan, and hydroxyethyl cellulose, or combinations thereof.

In another aspect, the invention includes a method of treating a gastrointestinal disorder in a patient in need thereof, consisting essentially of administering to the patient a composition comprising:
a) bismuth subsalicylate;
b) microcrystalline cellulose;
c) xanthan gum; and
d) an excipient selected from the group consisting of: carboxymethyl cellulose, carrageenan, and hydroxyethyl cellulose, or combinations thereof.

In one embodiment, said excipient is hydroxyethyl cellulose.

In one embodiment, said composition comprises bismuth subsalicylate in an amount of from about 10 mg/mL to about 60 mg/mL.

In one embodiment, said composition comprises bismuth subsalicylate in an amount of from about 17.5 mg/mL to about 53 mg/mL.

In another embodiment, said composition comprises bismuth subsalicylate in an amount of from about 15 mg/mL to about 20 mg/mL of the total composition.

In a further embodiment, said composition comprises bismuth subsalicylate in an amount of about 17.5 mg/mL.

In another embodiment, said composition comprises bismuth subsalicylate in an amount of about 32.5 mg/mL to about 37.5 mg/mL.

In a further embodiment, said composition comprises bismuth subsalicylate in an amount of about 35 mg/mL.

In one embodiment, said composition comprises bismuth subsalicylate in an amount of about 52.5 mg/mL.

In one embodiment, said composition comprises carboxymethyl cellulose and hydroxyethyl cellulose.

In one embodiment, said composition comprises xanthan gum in an amount of from about 0.50 mg/mL to about 5.0 mg/mL.

In a further embodiment, said composition comprises xanthan gum in an amount of from about 1.0 mg/mL to about 3.0 mg/mL.

In still a further embodiment, said composition comprises xanthan gum in an amount of about 2.0 mg/mL.

In another further embodiment, said composition comprises xanthan gum in an amount of about 2.9 mg/mL.

In one embodiment, said composition comprises hydroxyethyl cellulose in an amount of from about 0.45 mg/mL to about 2.0 mg/mL.

In a further embodiment, said composition comprises hydroxyethyl cellulose in an amount of about 1.5 mg/mL.

In one embodiment, said composition comprises a mixture of carboxymethyl cellulose and microcrystalline cellulose.

In a further embodiment, the mixture of carboxymethyl cellulose and microcrystalline cellulose is present in an amount of from about 14 mg/mL to about 20 mg/mL.

In still a further embodiment, the mixture of carboxymethyl cellulose and microcrystalline cellulose is present in an amount of about 17.1 mg/mL.

In another further embodiment, the mixture of carboxymethyl cellulose and microcrystalline cellulose is present in an amount of about 17.5 mg/mL.

In one embodiment, said composition has a sedimentation rate of from about 0.001 mm/day to about 0.015 mm/day as determined by x-ray measurement.

In a further embodiment, said composition has a sedimentation rate of from about 0.001 mm/day to about 0.012 mm/day as determined by x-ray measurement.

In one embodiment, said composition has a viscosity of from about 800 cps to about 2400 cps.

In a further embodiment, said composition has a viscosity of from about 1200 cps to about 2000 cps.

In one embodiment, said gastrointestinal disorder is selected from diarrhea, indigestion, heartburn, and nausea.

In one aspect, the invention includes a process for producing a composition described herein, comprising:

forming a gum premix comprising glycerin, simethicone, hydroxyethyl cellulose, and xanthan gum in a first vessel;

forming a dye premix comprising an aqueous mixture of dye compounds in a second vessel;

forming a third mixture comprising water, microcrystalline cellulose, carboxymethyl cellulose, and bismuth subsalicylate in a third vessel; and combining the gum premix, dye premix and third mixture together to produce the composition.

In one embodiment, the glycerin, simethicone, hydroxyethyl cellulose, and xanthan gum are added together and mixed for a time from about 5 minutes to about 15 minutes to form the gum premix.

In another embodiment, the glycerin, simethicone, hydroxyethyl cellulose, and xanthan gum are mixed for about 10 minutes to form the gum premix.

In one embodiment, the glycerin, simethicone, hydroxyethyl cellulose, and xanthan gum are mixed until homogenous to form the gum premix.

In one embodiment, the dye premix is a mixture of water, Red #22 D&C, and Red #28 D&C.

In a further embodiment, the dye premix is formed by adding Red #22 D&C, and Red #28 D&C to hot water.

In one embodiment, the third mixture is formed by a) combining water and a mixture of microcrystalline cellulose and carboxymethyl cellulose in the third vessel;

b) mixing until the mixture of microcrystalline cellulose and carboxymethyl cellulose is fully wetted;

c) mixing the fully wetted microcrystalline cellulose and carboxymethyl cellulose for at least 5 minutes;

d) shearing the fully wetted microcrystalline cellulose and carboxymethyl cellulose from step c;

e) adding bismuth subsalicylate and water to the third vessel;

f) mixing until the bismuth subsalicylate is fully wetted; and g) mixing the resulting mixture for at least an additional 5 minutes.

In a further embodiment, step b further comprises two or more separate additions of water.

In another further embodiment, the mixing in steps c and g are each about 15 minutes.

In another further embodiment, the mixture of microcrystalline cellulose and carboxymethyl cellulose is commercially available as AVICEL RC-591.

In one embodiment, the gum premix is combined with the third mixture in the third vessel prior to combining the dye premix.

In a further embodiment, the gum premix and third mixture are mixed for at least 20 minutes.

In still a further embodiment, the gum premix and third mixture are mixed for about 30 minutes.

In still a further embodiment, the resulting mixture is combined with the dye premix, salicylic acid, sodium salicylate, sodium saccharin, potassium sorbate, glycerin, and methylsalicylate in the third mixing vessel.

In still a further embodiment, water is added to the resulting mixture in the third mixing vessel and the resulting mixture was mixed.

In still a further embodiment, the resulting mixture was mixed for about 15 minutes.

EXAMPLES

Example 1: Methods of Batch Preparation

Pharmaceutical formulations of the present invention may generally be prepared according to one of three general methods as provided below.

Method a Batch Procedure

Gum Premix

Glycerin (35.00 g) was added to the gum premix vessel. Xanthan gum (2.00 g) was then added to the gum premix vessel and mixed for 10 minutes to disperse.

Dye Premix 10 g of hot purified water was added to a dye premix vessel. Then Red #22 D&C (0.0563 g) and Red #28 D&C (0.04814 g) were added to the dye premix vessel and mixed for 10 minutes.

Batch Mix

A batch was created by addition of 930 g of cold water to a mixing vessel. Then 17.07 g Avicel RC-591 was added to the mixing vessel. The mixture was sheared for three minutes (equivalent of 2.1 turns). While shearing, the contents of the gum premix vessel and the bismuth subsalicylate (17.50 g) was added to the batch and sheared for an additional two minutes. The shearing was stopped, and the batch was mixed for 30 minutes while the gums fully hydrated. Then, 0.01 g salicylic acid, 0.68 g sodium salicylate, 0.41 g sodium saccharin, 0.38 g sorbic acid and the contents of the dye premix vessel were added to the batch. Purified water was then added to a final volume of one liter, and the batch was then mixed for an additional 15 minutes.

Samples 1-43 were prepared according to Method A. Every sample contained 0.41 g sodium saccharin, 0.38 g sorbic acid, 0.0563 g red #22 D&C, 0.0492 g red #28 D&C, and 1.00 g methylsalicylate. The other ingredients were added in amounts according to Tables 1a-8b below. All amounts in Tables 1a-8b are provided in grams.

TABLE 1a

Compositions prepared according to Method A batch procedure.

| Sample | water | AVICEL | glycerin | Xanthan gum |
|---|---|---|---|---|
| 1 | 917.97 | 30.00 | 50.00 | 2.30 |
| 2 | 976.43 | 12.24 | 10.00 | 1.22 |
| 3 | 956.43 | 12.24 | 30.00 | 1.22 |
| 4 | 947.34 | 19.55 | 30.00 | 3.00 |
| 5 | 954.34 | 12.73 | 30.00 | 2.82 |
| 6 | 957.62 | 10.00 | 30.00 | 2.27 |
| 7 | 946.89 | 20.91 | 30.00 | 2.09 |
| 8 | 956.98 | 11.36 | 30.00 | 1.55 |
| 9 | 950.35 | 18.18 | 30.00 | 1.36 |
| 10 | 954.8 | 14.09 | 30.00 | 1.00 |
| 11 | 952.53 | 15.45 | 30.00 | 1.91 |
| 12 | 943.61 | 23.64 | 30.00 | 2.64 |
| 13 | 946.44 | 22.27 | 30.00 | 1.18 |
| 14 | 950.62 | 16.82 | 30.00 | 2.45 |
| 15 | 943.16 | 25.00 | 30.00 | 1.73 |
| 16 | 947.89 | 20.00 | 30.00 | 2.00 |

TABLE 1b

Compositions prepared according to Method A batch procedure continued.

| Sample | bismuth subsalicylate | salicylic acid | sodium salicylate | pH | Viscosity (cp) |
|---|---|---|---|---|---|
| 1 | 17.50 | 0.52 | 0.20 | 4.353 | 3000 |
| 2 | 17.50 | 0.52 | 0.20 | 3.523 | 204 |
| 3 | 17.50 | 0.52 | 0.20 | 3.559 | 188 |
| 4 | 17.50 | 0.52 | 0.20 | 3.838 | 1060 |
| 5 | 17.50 | 0.52 | 0.20 | 3.646 | 583.9 |
| 6 | 17.50 | 0.52 | 0.20 | 3.553 | 279.9 |
| 7 | 17.50 | 0.52 | 0.20 | 3.798 | 711.84 |
| 8 | 17.50 | 0.52 | 0.20 | 3.473 | 204 |
| 9 | 17.50 | 0.52 | 0.20 | 3.709 | 355.9 |
| 10 | 17.50 | 0.52 | 0.20 | 3.488 | 176 |
| 11 | 17.50 | 0.52 | 0.20 | 3.599 | 407.9 |
| 12 | 17.50 | 0.52 | 0.20 | 3.772 | 1048 |
| 13 | 17.50 | 0.52 | 0.20 | 3.731 | 499.9 |
| 14 | 17.50 | 0.52 | 0.20 | 3.674 | 651.9 |
| 15 | 17.50 | 0.52 | 0.20 | 3.788 | 959.8 |
| 16 | 17.50 | 0.42 | 0.30 | 3.806 | 723.8 |

TABLE 2a

CMC 12 compositions prepared according to Method A batch procedure.

| Sample | water | AVICEL | glycerin | Xanthan gum | CMC 12M31F |
|---|---|---|---|---|---|
| 17 | 956.08 | 11.36 | 30.00 | 1.55 | 1.00 |

TABLE 2b

CMC 12 compositions prepared according to Method A batch procedure continued.

| Sample | bismuth subsalicylate | salicylic acid | sodium salicylate | pH | Viscosity (cp) |
|---|---|---|---|---|---|
| 17 | 17.50 | 0.42 | 0.20 | 3.845 | 243.9 |

TABLE 3a

CMC 9 compositions prepared according to Method A batch procedure.

| Sample | water | AVICEL | glycerin | Xanthan gum | CMC 9M31F |
|---|---|---|---|---|---|
| 18 | 945.89 | 20.00 | 30.00 | 2.00 | 2.00 |

TABLE 3b

CMC 9 compositions prepared according to Method A batch procedure continued.

| Sample | bismuth subsalicylate | salicylic acid | sodium salicylate | pH | Viscosity (cp) |
|---|---|---|---|---|---|
| 18 | 17.50 | 0.42 | 0.30 | 4.164 | 1648 |

TABLE 4a

Carageenan compositions prepared according to Method A batch procedure.

| Sample | water | AVICEL | glycerin | Xanthan gum | Carrageenan Special |
|---|---|---|---|---|---|
| 21 | 942.89 | 20.00 | 30.00 | 2.00 | 5.00 |

TABLE 4b

Carageenan compositions prepared according to Method A batch procedure continued.

| Sample | bismuth subsalicylate | salicylic acid | sodium salicylate | pH | Viscosity (cp) |
|---|---|---|---|---|---|
| 21 | 17.50 | 0.42 | 0.30 | 3.720 | 939.8 |

TABLE 5a

HEC and simethicone compositions prepared according to Method A batch procedure.

| Sample | water | AVICEL | glycerin | HEC 250 G | Xanthan gum | Simethicone emulsion |
|---|---|---|---|---|---|---|
| 22 | 941.88 | 25.50 | 30.00 | 0.50 | 2.00 | 0.01 |
| 23 | 947.37 | 20.00 | 30.00 | 0.50 | 2.00 | 0.02 |

TABLE 5b

HEC and simethicone compositions prepared according to Method A batch procedure continued.

| Sample | bismuth subsalicylate | salicylic acid | sodium salicylate | pH | Viscosity (cp) |
|---|---|---|---|---|---|
| 22 | 17.50 | 0.13 | 0.59 | 4.296 | 1968 |
| 23 | 17.50 | 0.13 | 0.59 | 4.329 | 1716 |

TABLE 6a

CMC 9 and simethicone compositions prepared
according to Method A batch procedure.

| Sample | water | AVICEL | glycerin | CMC 9M31F | Xanthan gum | Simethicone emulsion |
|--------|-------|--------|----------|-----------|-------------|----------------------|
| 24 | 946.37 | 20.00 | 30.00 | 1.50 | 2.00 | 0.02 |

TABLE 6b

CMC 9 and simethicone compositions prepared according
to Method A batch procedure continued.

| Sample | bismuth subsalicylate | salicylic acid | sodium salicylate | pH | Viscosity (cp) |
|--------|----------------------|----------------|-------------------|------|----------------|
| 24 | 17.50 | 0.13 | 0.59 | 4.455 | 2839 |

TABLE 7a

HEC compositions prepared according
to Method A batch procedure.

| Sample | water | AVICEL | glycerin | HEC 250 G | Xanthan gum |
|--------|-------|--------|----------|-----------|-------------|
| 25 | 947.39 | 20.00 | 30.00 | 0.50 | 2.00 |
| 26 | 940.91 | 25.50 | 30.00 | 1.50 | 2.00 |
| 27 | 957.31 | 10.00 | 30.00 | 0.10 | 2.00 |
| 28 | 955.91 | 10.00 | 30.00 | 1.50 | 2.00 |
| 29 | 949.36 | 17.75 | 30.00 | 0.80 | 2.00 |
| 30 | 942.81 | 25.50 | 30.00 | 0.10 | 2.00 |
| 31 | 957.81 | 10.00 | 30.00 | 0.10 | 2.00 |
| 32 | 942.31 | 25.50 | 30.00 | 0.10 | 2.00 |
| 33 | 940.91 | 25.50 | 30.00 | 1.50 | 2.00 |
| 34 | 956.91 | 10.00 | 30.00 | 1.50 | 2.00 |
| 35 | 940.41 | 25.50 | 30.00 | 1.50 | 2.00 |
| 36 | 942.31 | 25.50 | 30.00 | 0.10 | 2.00 |
| 37 | 957.81 | 10.00 | 30.00 | 0.10 | 2.00 |
| 38 | 949.97 | 17.07 | 30.00 | 0.88 | 2.00 |
| 39 | 949.77 | 17.07 | 30.00 | 0.88 | 2.20 |
| 40 | 949.97 | 17.07 | 30.00 | 0.88 | 2.00 |
| 41 | 949.97 | 17.07 | 30.00 | 0.88 | 2.00 |

TABLE 7b

HEC compositions prepared according to
Method A batch procedure continued.

| Sample | bismuth subsalicylate | salicylic acid | sodium salicylate | pH | Viscosity (cp) |
|--------|----------------------|----------------|-------------------|------|----------------|
| 25 | 17.50 | 0.13 | 0.59 | 4.323 | 1612 |
| 26 | 17.50 | 0.10 | 0.60 | 4.438 | 2450 |
| 27 | 17.50 | 0.60 | 0.60 | 3.535 | 280 |
| 28 | 17.50 | 0.60 | 0.60 | 3.542 | 428 |
| 29 | 17.50 | 0.35 | 0.35 | 3.967 | 856 |
| 30 | 17.50 | 0.10 | 0.10 | 4.360 | 2248 |
| 31 | 17.50 | 0.60 | 0.10 | 3.424 | 264 |
| 32 | 17.50 | 0.10 | 0.60 | 4.359 | 1920 |
| 33 | 17.50 | 0.60 | 0.10 | 3.774 | 1416 |
| 34 | 17.50 | 0.10 | 0.10 | 4.074 | 448 |
| 35 | 17.50 | 0.60 | 0.60 | 3.836 | 1676 |
| 36 | 17.50 | 0.60 | 0.10 | 3.719 | 1008 |
| 37 | 17.50 | 0.10 | 0.60 | 4.089 | 348 |
| 38 | 17.50 | 0.01 | 0.68 | 4.398 | 1052 |
| 39 | 17.50 | 0.01 | 0.68 | 4.462 | 1064 |
| 40 | 35.00 | 0.01 | 0.68 | 4.300 | 1048 |
| 41 | 52.50 | 0.01 | 0.68 | 4.263 | 1072 |

TABLE 8a

Simethicone compositions prepared according
to Method A Batch Procedure.

| Sample | water | AVICEL | glycerin | Xanthan gum | Simethicone emulsion |
|--------|-------|--------|----------|-------------|----------------------|
| 42 | 947.88 | 20.00 | 30.00 | 2.00 | 0.01 |
| 43 | 942.38 | 25.50 | 30.00 | 2.00 | 0.01 |

TABLE 8b

Simethicone compositions prepared according
to Method A Batch Procedure continued.

| Sample | bismuth subsalicylate | salicylic acid | sodium salicylate | pH | Viscosity (cp) |
|--------|----------------------|----------------|-------------------|------|----------------|
| 42 | 17.50 | 0.42 | 0.30 | 3.796 | 771.8 |
| 43 | 17.50 | 0.13 | 0.59 | 4.237 | 1396 |

Method B Batch Procedure

A Waukesha Shear Pump inlet was connected to the outlet of a mix tank. The Waukesha Shear Pump outlet was placed on the rim of the mix tank to allow for recirculation down the wall of the tank. Then, 173.0 kg cold purified water was added to the mix tank. The baffles were set to at or between 0° and 90° and the agitator was turned on. The agitator was adjusted to 140 RPM.

While continuing the mix, 3.00 kg glycerin USP was added to a hydroxyethyl cellulose mix tank and agitation was started. Then hydroxyethyl cellulose 250G (176 g) was added and mixed for 5 minutes. The mixing was continued until hydroxyethyl cellulose was added.

Glycerin (3.00 kg) was added to a xanthan gum premix tank and agitation was started. Then, xanthan Gum (0.400 kg) was added and mixed for 5 minutes. Mixing was continued.

Avicel RC-591 (3.41 kg) was added to the mix tank. The interior of the tank was rinsed with 5.0 kg cold purified water. The mix tank outlet was opened and the shear pump started, recirculating back into the mix tank. The mix tank was recirculated, until the product was homogeneous. Then, 2.00 g of simethicone emulsion was added to the mix tank. The contents of the hydroxyethyl cellulose mix tank were then added to the mix tank. The contents of the xanthan gum premix tank were then added to the mix tank.

Bismuth subsalicylate USP (3.50 kg) was added to the mix tank. The surface of the batch was sprayed with 10.0 kg cold purified water to wet the material. The mix tank was recirculated for 10 minutes, until the product was homogeneous. The mix tank outlet was closed and the shear pump was stopped. 1.00 kg glycerin USP was added to the mix tank. Salicylic acid (2.00 g), sodium salicylate (136 g), sodium saccharin (82 g), and sorbic acid (76.0 g) were added to the mix tank. The tank walls and mixer shaft were then washed with 1.0 kg cold water.

3.0 kg of hot purified water was then added to the dye premix. Then Red #22 D&C (9.63 g) followed by red #28 D&C (9.63 g) to the dye premix. The dye mixture was then mixed for 2 minutes.

The dye mixture was added to the mix tank. The dye premix tank was then rinsed with 1.0 kg hot purified water, and the water was added to the mix tank. The mix tank was cooled to less than 30° C., and the jackets were drained. Methylsalicylate (200 g) was then added to the mix tank. The container of methylsalicylate was then rinsed with 1.0 kg cold purified water, and the water was added to the mix tank. The batch was mixed for 15 minutes. The solution was transferred to a hold tank with an attached impeller blade through the Waukesha Shear Pump. The solution was held for 2 hours while mixing at 200 rpm. The agitator was turned off and the jackets were drained.

Method C Batch Procedure

Gum Premix 25.5 g Glycerin, 0.01 g Simethicone, 1.50 g hydroxyethyl cellulose, and 2.90 g Xanthan Gum were added to a premix vessel and mixed for 10 minutes.

Dye Premix 10 g of hot purified water was added to a dye premix vessel. Then Red #22 D&C (0.0563 g) and Red #28 D&C (0.04814 g) were added to the dye premix vessel and mixed for 10 minutes.

Batch Mix

A batch was created by the addition of 555 g cold water and 17.50 g AVICEL RC-591 to a mixing vessel. The batch was rinsed and fully wetted with an additional 70 g cold water, and then mixed for 15 minutes. The batch was then sheared for 3 minutes (equivalent of 2.1 turns). 17.50 g bismuth subsalicylate USP was then added and fully wetted with an additional 300 g cold water. The batch was mixed for 15 minutes. The gum premix was then added, and the batch mixed for an additional 30 minutes. The dye premix, 0.20 g salicylic acid, 0.01 g sodium salicylate, 0.41 g sodium saccharin, 0.35 g potassium sorbate, 9.5 g glycerin, and 1.0 g methylsalicylate were then added to the batch. Purified water was then added to a total volume of one liter, and then the batch was mixed for an additional 15 minutes.

Example 2: Comparison of Selected Formulations of the Invention with Commercial Products Sample formulations were prepared according to the Method A batch procedure described in Example 1. Amounts of Avicel, xanthan gum, hydroxyethyl cellulose, and bismuth subsalicylate were provided in the amounts shown in Table 9 below as Samples E-J and compared against commercially available products (Samples A-D). Sample J also included simethicone.

Example 3: Rheometer Procedure and Rheogram Results

Rheograms of pharmaceutical compositions of the present invention were taken according to the following procedure. A quantity of suspension (~2 mL) was placed on a flat plate of the rheometer. The base of the was raised to a gap distance of 0.7 mm to a rotating spindle plate. The temperature was equilibrated to 25° C. and the top plate was rotated at a slow speed with a ram to a higher speed for five minutes. The speed was held for 30 seconds and then the top plate speed was reduced over five minutes. During the slowing the rheometer records the resistance to rotation (torque) with respect to time.

Figure 2:
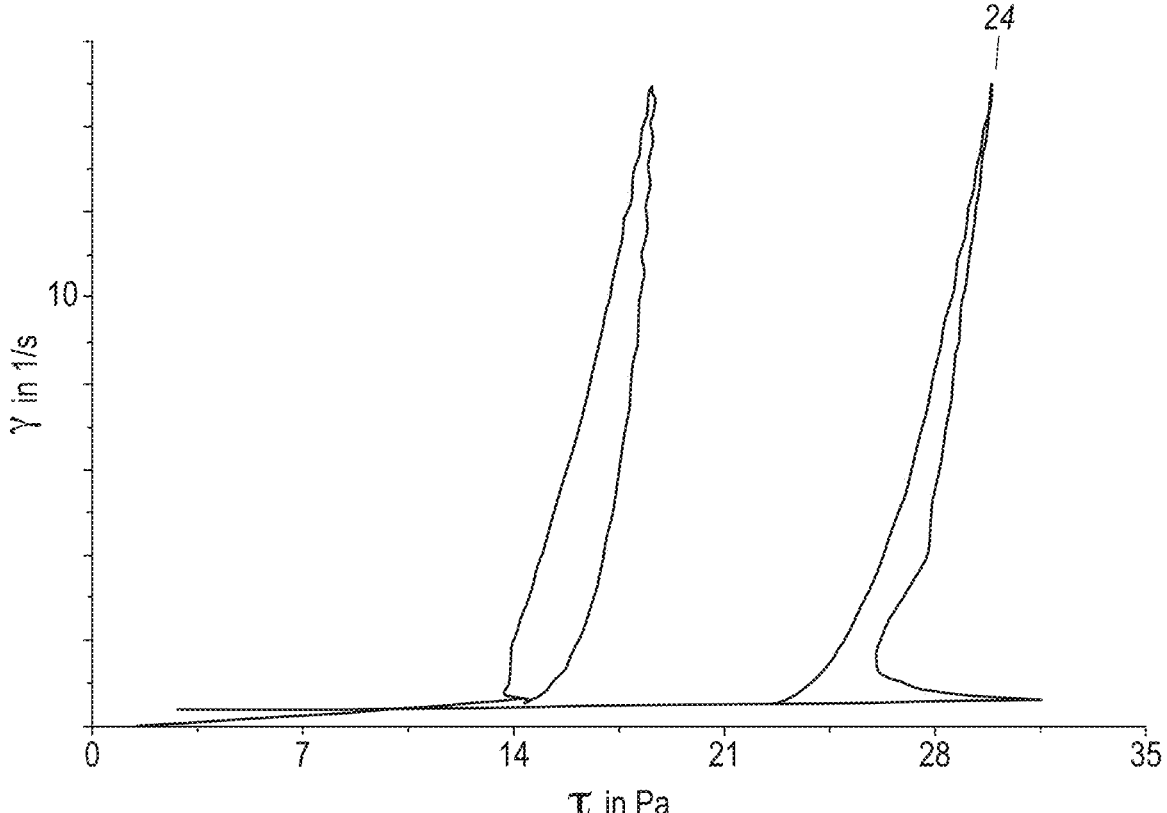
FIG. 2 shows a rheogram of sample composition 24 according to an embodiment of the present invention.
Figure 3:
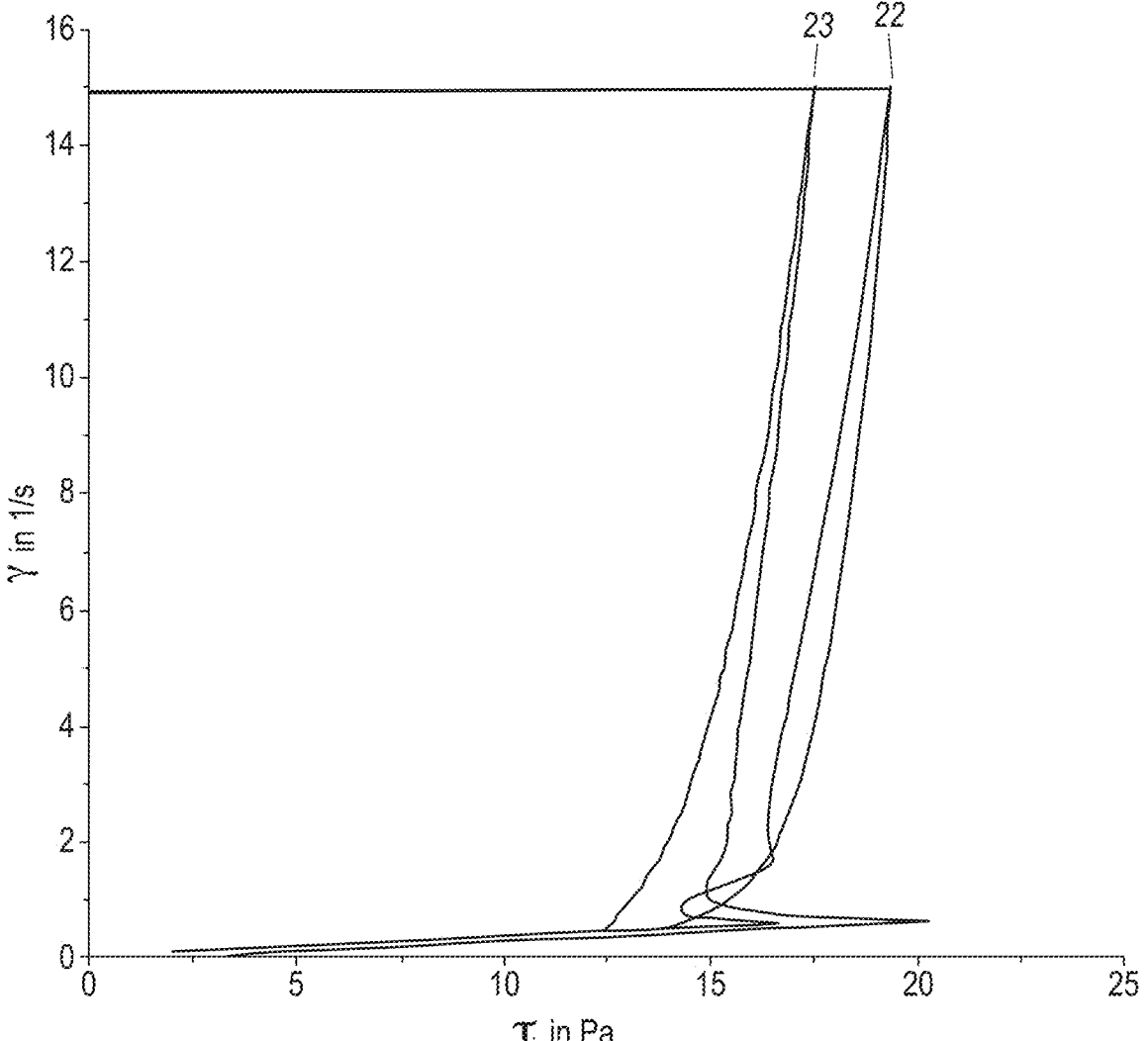
FIG. 3 shows a rheogram comparing sample compositions 22 and 23 according to an embodiment of the present invention.

Rheograms may be used to determine whether pharmaceutical compositions of the present invention have appropriate shear stress and shear flow for consumer use. Rheograms of pharmaceutical compositions according to the following formulations are shown in FIGS. 1-3.

Example 4: Dispersion Fingerprints

The dispersion of Samples A-I were tested using a LUMi-Sizer®650. Samples A-I were analyzed at start and final times. Dispersion fingerprints of Samples A-I were tested. Results of the dispersion fingerprints are shown in FIG. 4.

Example 5: Sedimentation Analysis

Figures 5A, 5B, 5C, 5D, 5E, 5F:
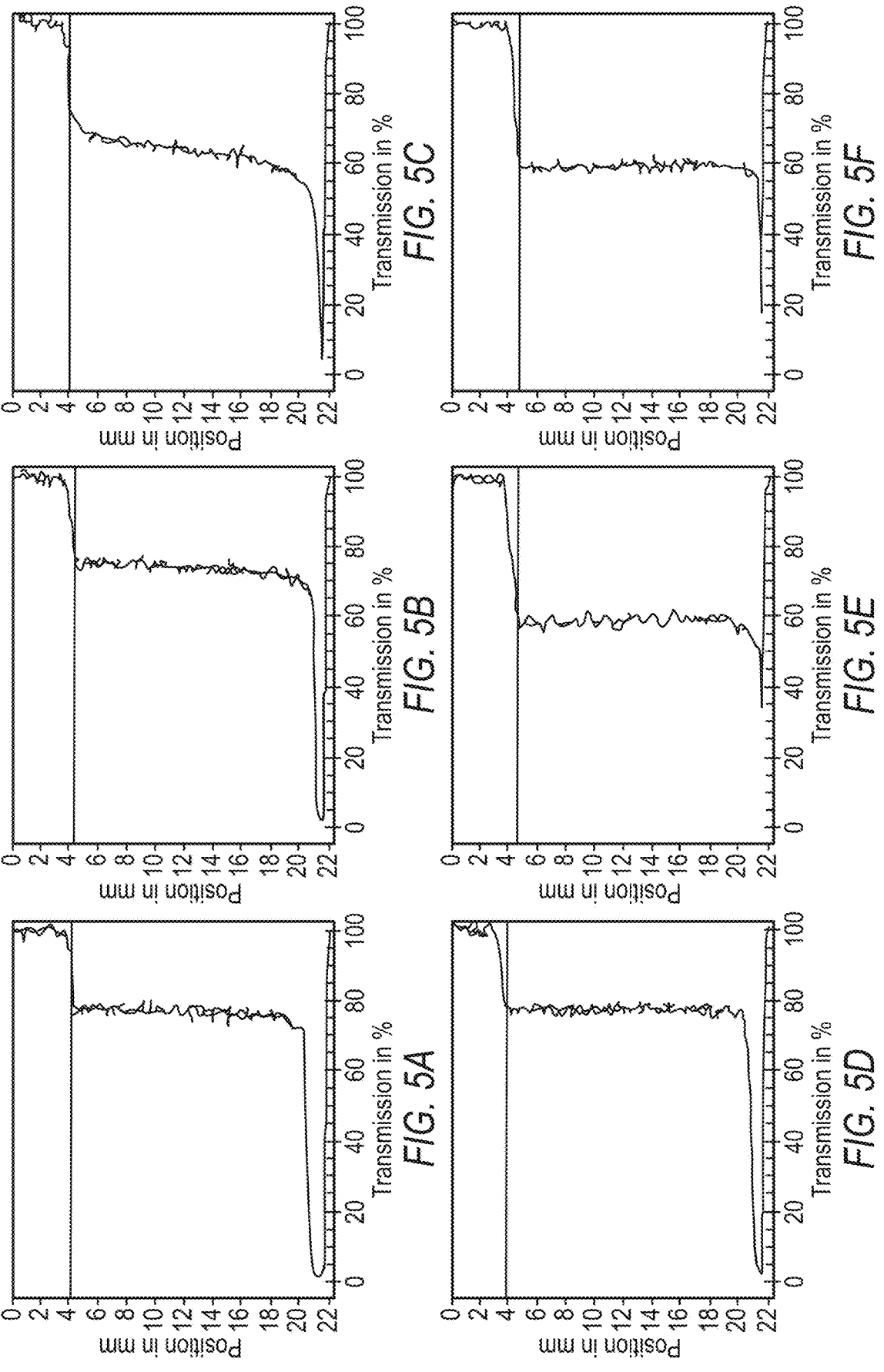

Sedimentation rates and sedimentation fingerprints of selected compositions of the invention were determined by X-Ray analysis using a LUMiReader X-Ray. Sedimentation fingerprints of Samples A-J are provided in FIG. 5, and sedimentation rates are provided in Table 10 below.

TABLE 9

Sample formulations containing bismuth subsalicylate.

| Sample | Description | Veegum | Methocel | Avicel (mg/L) | Xanthan (mg/L) | HEC (mg/L) | Bismuth Subsalicylate (mg/L) |
|--------|-------------|--------|----------|---------------|----------------|------------|------------------------------|
| A | Comparison 1 | yes | yes | no | no | no | 0.01750 |
| B | Comparison 2 | yes | yes | no | yes | no | 0.01750 |
| C | Comparison 3 | no | no | no | yes | yes | 0.01750 |
| D | Comparison 4 | yes | yes | no | no | no | 0.01750 |
| E | Embodiment 1 | no | no | 0.01707 | 0.00200 | 0.00088 | 0.01750 |
| F | Embodiment 2 | no | no | 0.01707 | 0.00220 | 0.00088 | 0.01750 |
| G | Embodiment 3 | no | no | 0.01707 | 0.00200 | 0.00088 | 0.03500 |
| H | Embodiment 4 | no | no | 0.02000 | 0.00200 | 0.00050 | 0.01750 |
| I | Embodiment 5 | no | no | 0.01707 | 0.00200 | 0.00088 | 0.05250 |
| J | Embodiment 6 | no | no | 0.01707 | 0.00200 | 0.00088 | 0.01750 |

TABLE 10

| | Sediment formation rate of Samples A-J as determined by X-Ray analysis. | |
|---|---|---|
| Sample | | Sediment Formation Rate (mm/day) |
| A | | 0.0353 |
| B | | 0.0178 |
| C | | 0.0102 |
| D | | 0.0212 |
| E | | 0.0052 |
| F | | 0.0041 |
| G | | 0.0267 |
| H | | 0.0119 |
| I | | 0.0620 |
| J | | 0.0286 |

Example 6: Sedimentation Comparison to Commercial Products

Figure 6:
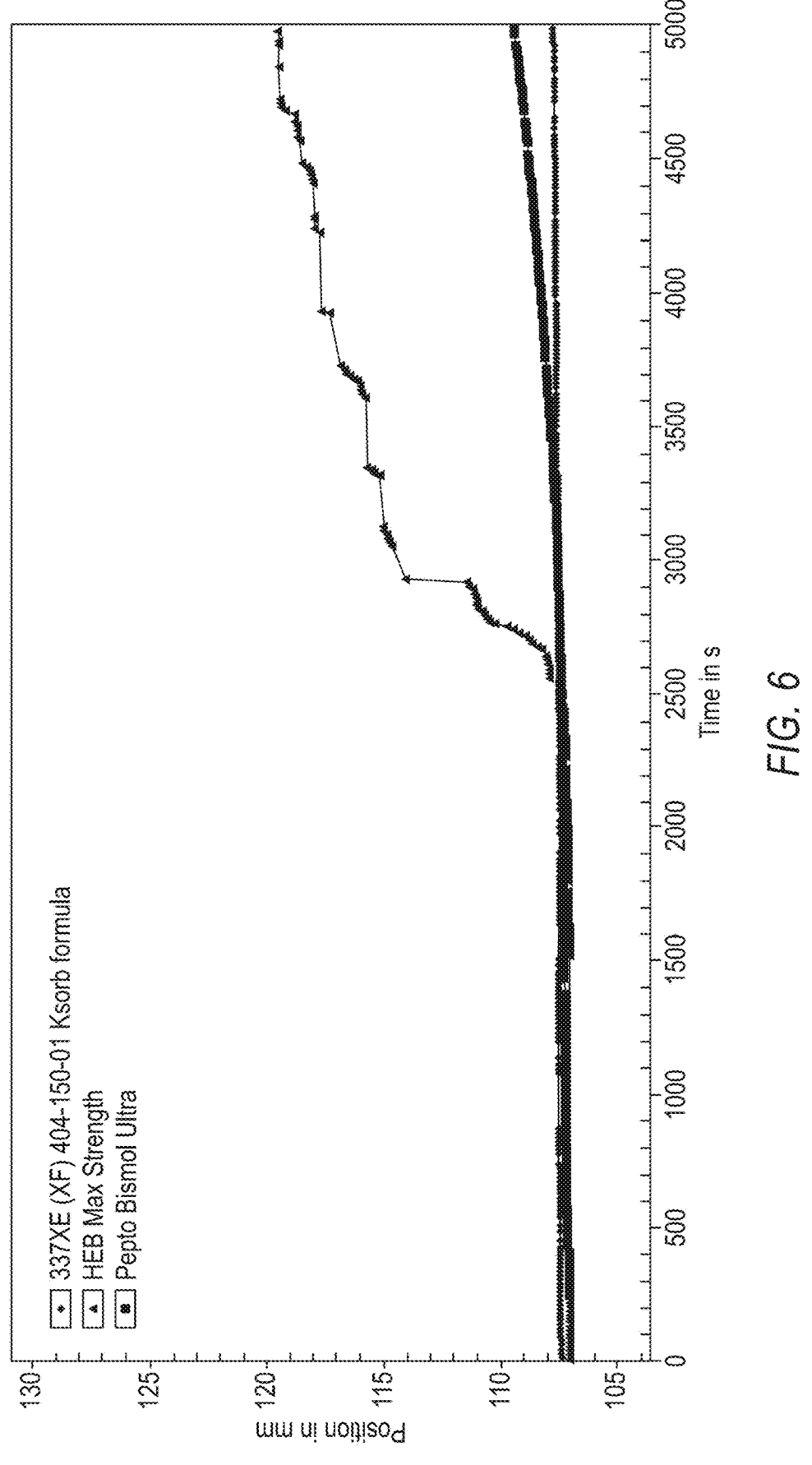
FIG. 6 is a plot comparing the sedimentation profiles of the composition of Method C (diamonds), the commercially available H.E.B. Max Strength (triangles), and the commercially available Pepto Bismol Ultra (squares)

The sedimentation profiles of the composition of Method C, the commercially available H.E.B. Max Strength, and the commercially available Pepto Bismol Ultra were obtained using an 8-channel LUMiFuge 1103-28 at a spin rate of 4,000 RPM. FIG. 6 provides evidence that the composition of Method C is more resistant to sedimentation under the test conditions than either commercial product. From the figure it can be seen that no significant sedimentation of the composition of Method C takes place over a time period of 5,000 seconds.

Figure 7A:
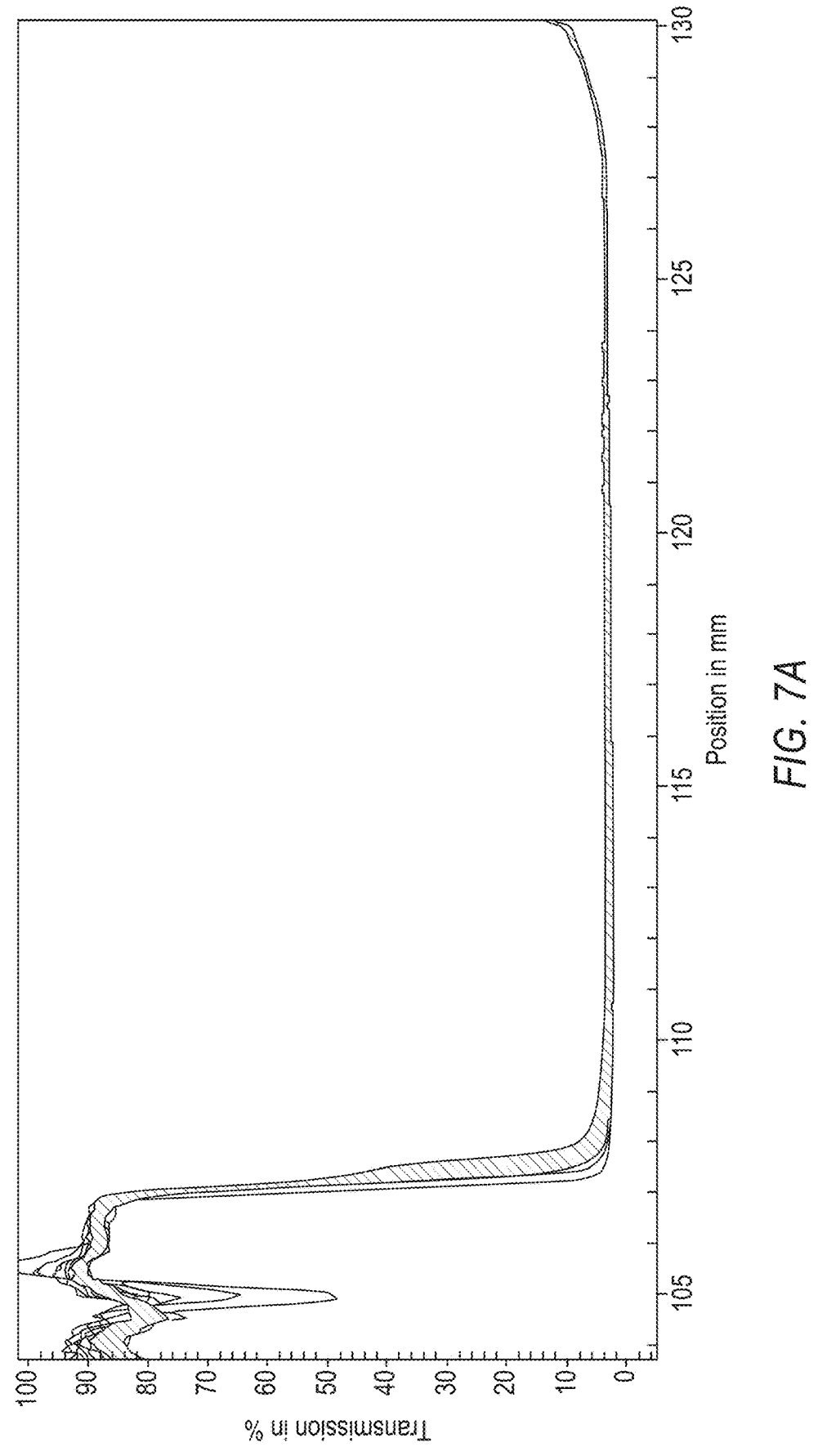
FIG. 7A is a sedimentation fingerprint of the composition of Method C.
Figure 7B:
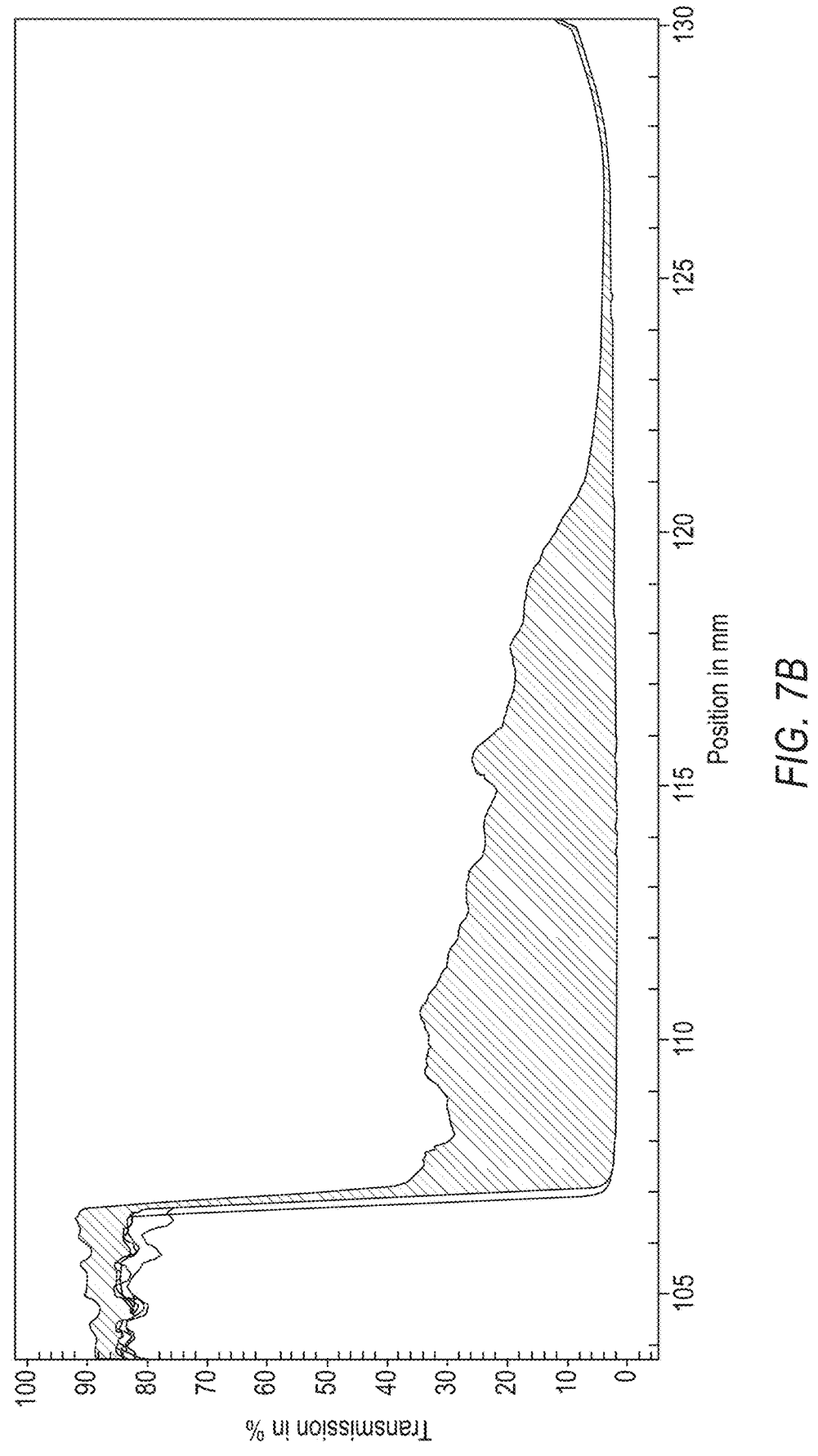
FIG. 7B is a sedimentation fingerprint of the commercially available H.E.B. Max Strength.
Figure 7C:
FIG. 7C is a sedimentation fingerprint of the commercially available Pepto Bismol Ultra.

Sedimentation fingerprints of the composition of Method C, the commercially available H.E.B. Max Strength, and the commercially available Pepto Bismol Ultra, which were obtained using the same instrument, also at a spin rate of 4,000 RPM over 5,000 seconds, are provided in FIGS. 7A-7C.

Example 7: Sedimentation Profile of a Bulk Batch

Figure 8:
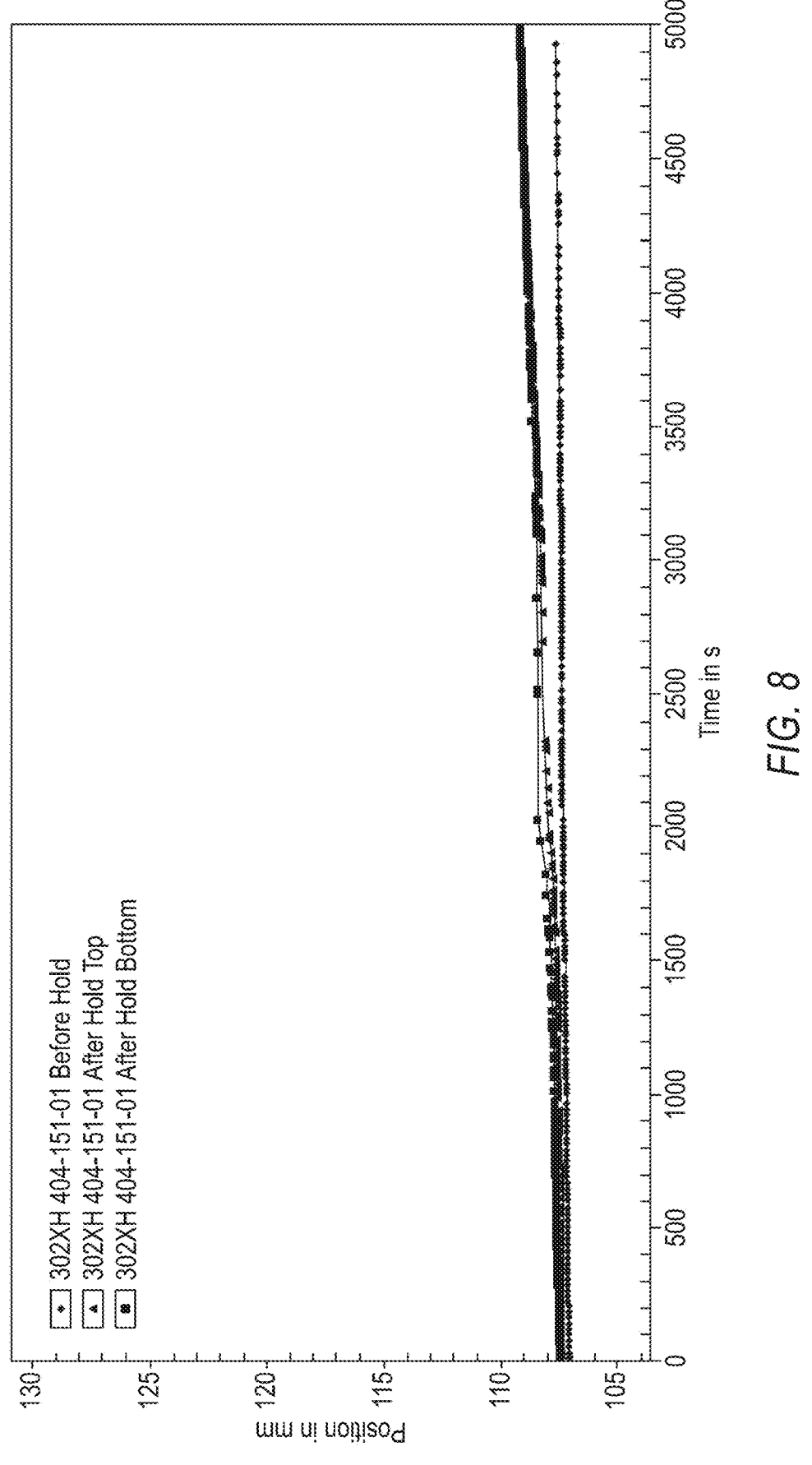
FIG. 8 is a plot of the sedimentation profile of a 1037.6 g batch of the composition of Method C.

The sedimentation profile of a 1037.6 g batch of the composition of Method C was obtained using an 8-channel LUMiFuge 1103-28 at a spin rate of 4,000 RPM. Following the Method C batch procedure to produce the 1037.6 g batch, as described herein, a sample was taken and tested immediately after the batch was produced (Sample Before Hold). The bulk batch was then held in a single vessel for 7 days, after which a sample was taken and tested from the top of the batch (near the surface of the composition—Top Sample After Hold), and another sample was taken and tested from the bottom of the batch (Bottom Sample After Hold). FIG. 8 provides the comparison of the sedimentation profiles of the three samples. The sedimentation rate of the Sample Before Hold (diamonds) is 0.1177 μm/min, the sedimentation rate of the Top Sample After Hold (triangles) is 0.03629 μm/min, and the sedimentation rate of the Bottom Sample After Hold (squares) is 0.03830 μm/min.

Figure 9A:
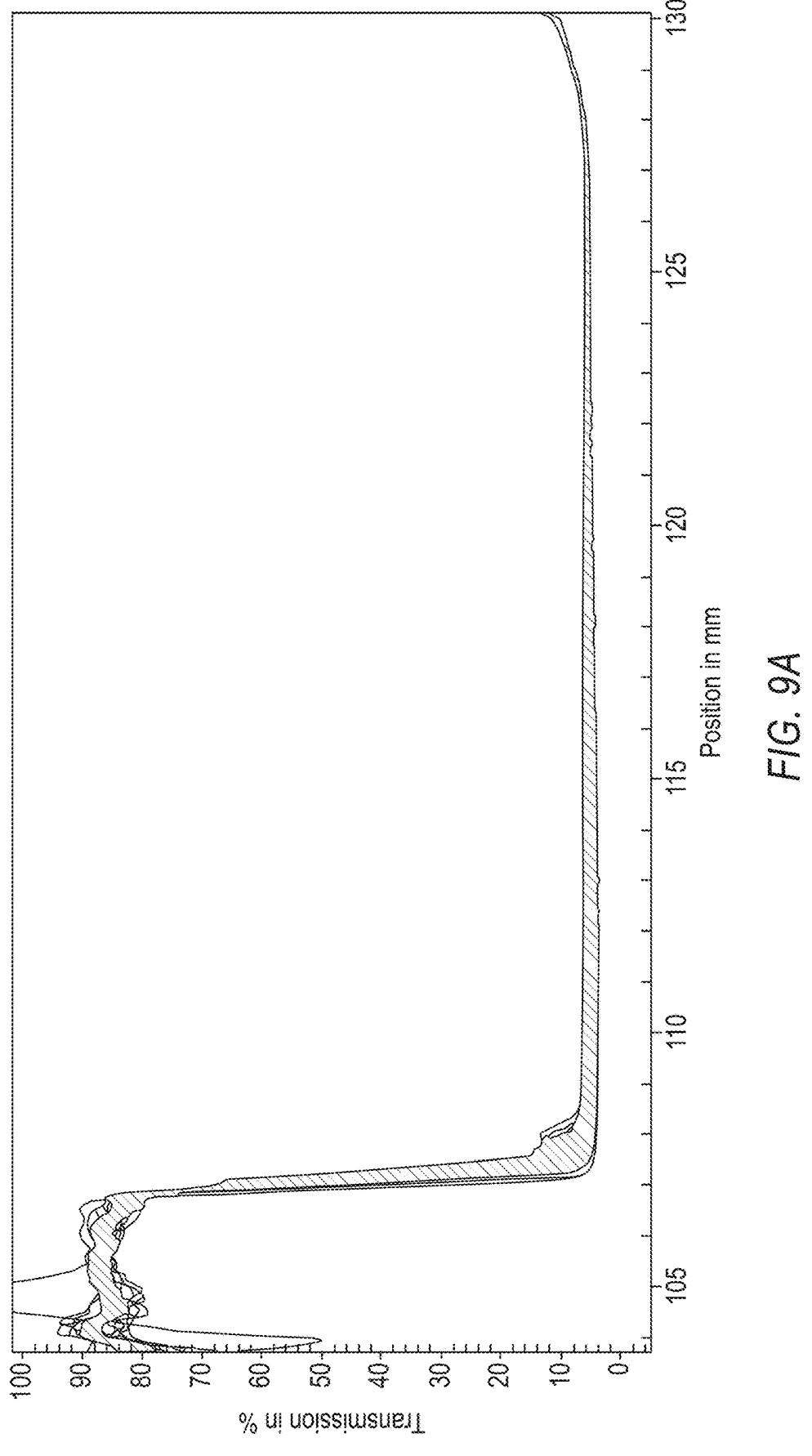
FIG. 9A is a sedimentation fingerprint of the Sample Before Hold from a 1037.6 g batch of the composition of Method C.
Figure 9B:
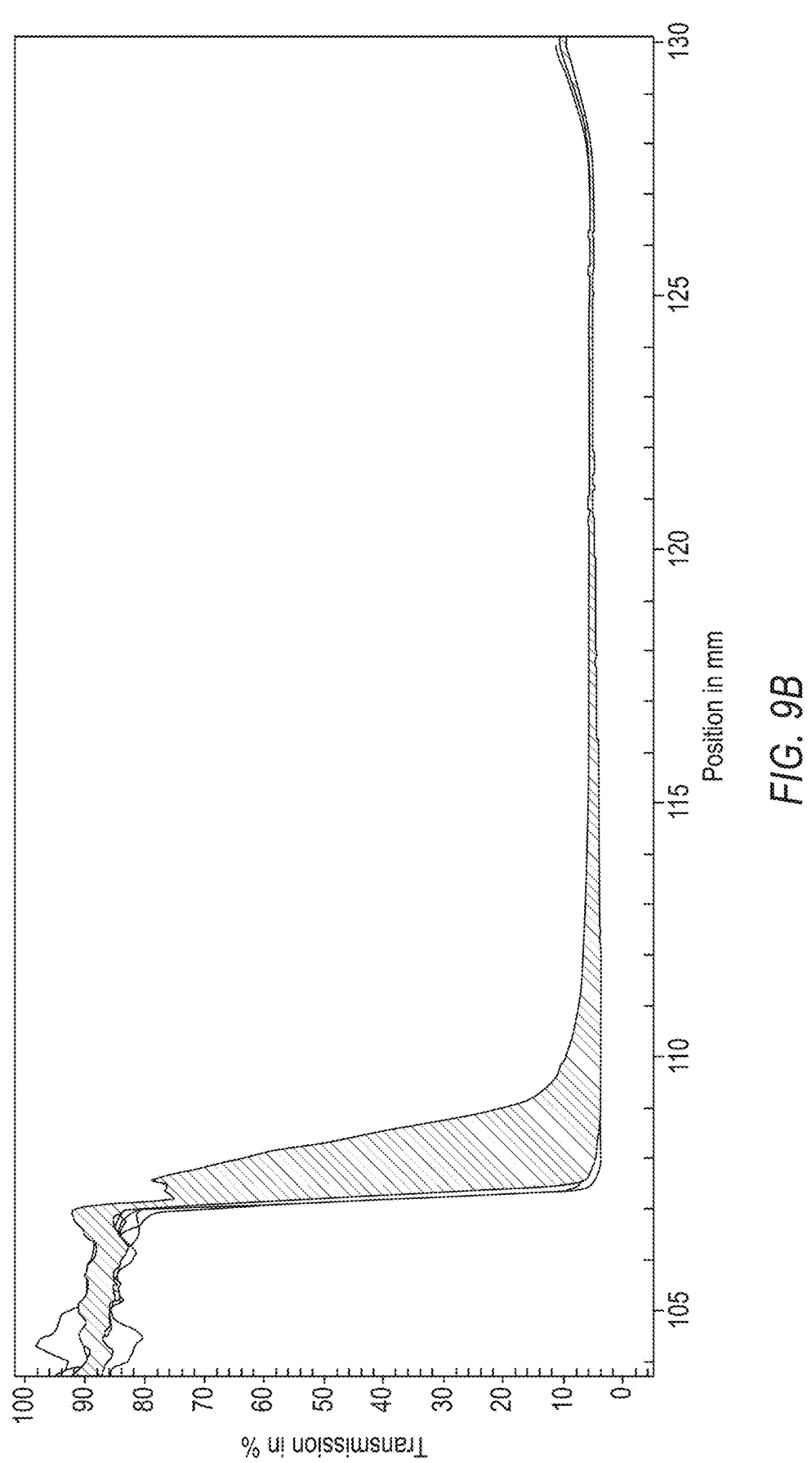
FIG. 9B is a sedimentation fingerprint of the Top Sample After Hold from a 1037.6 g batch of the composition of Method C.
Figure 9C:
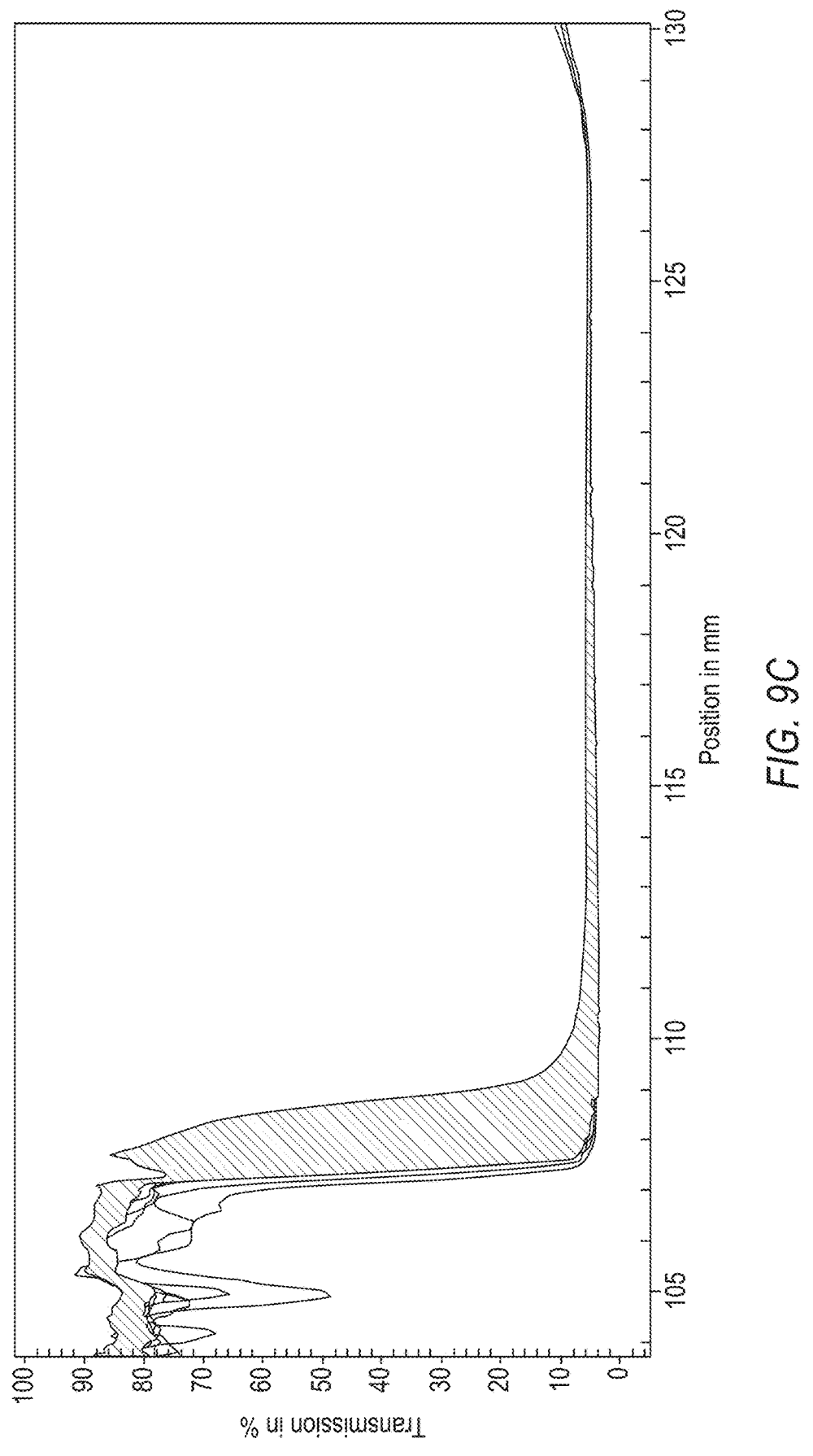
FIG. 9C is a sedimentation fingerprint of the Bottom Sample After Hold from a 1037.6 g batch of the composition of Method C.

Sedimentation fingerprints of the Sample Before Hold, Top Sample After Hold, and Bottom Sample After Hold, which were obtained using the same instrument, also at a spin rate of 4,000 RPM over 5,000 seconds, are provided in FIGS. 9A-9C.

Other Embodiments

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The invention claimed is:

1. A pharmaceutical composition, wherein the composition is a three-gum system, consisting essentially of:
   a) 17.5 mg/mL bismuth subsalicylate;
   b) 2.9 mg/mL xanthan gum;
   c) 1.5 mg/mL hydroxyethyl cellulose; and
   d) 17.5 mg/mL a mixture of microcrystalline cellulose and carboxymethyl cellulose.

2. A method of treating a gastrointestinal disorder in a patient in need thereof, comprising administering to the patient a composition according to claim 1.

3. The composition of claim 1, wherein said composition has a sedimentation rate of from 0.001 mm/day to 0.015 mm/day at 23° C. as determined by x-ray measurement.

4. The composition of claim 1, wherein said composition has a viscosity of from 800 cps to 2400 cps, and the pH of the composition is from 4.0 to 5.5.

\* \* \* \* \*